United States Patent [19]
Kasori et al.

[11] Patent Number: 5,908,922
[45] Date of Patent: Jun. 1, 1999

[54] METHOD FOR PRODUCING A SUCROSE FATTY ACID ESTER

[75] Inventors: Yukio Kasori, Tokyo; Keita Kashiwa, Toho-cho, both of Japan

[73] Assignee: Mitsubishi Chemical Corporation, Tokyo, Japan

[21] Appl. No.: 08/829,937

[22] Filed: Apr. 1, 1997

[30] Foreign Application Priority Data

Apr. 2, 1996 [JP] Japan .................................. 8-079813

[51] Int. Cl.$^6$ .................................................. C07H 15/00
[52] U.S. Cl. ........................................ 536/18.6; 536/18.5
[58] Field of Search .................... 536/18.5, 18.6

[56] References Cited

U.S. PATENT DOCUMENTS

| | | | |
|---|---|---|---|
| 4,611,055 | 9/1986 | Yamamoto et al. | 536/119 |
| 4,966,966 | 10/1990 | Wada et al. | 536/119 |

FOREIGN PATENT DOCUMENTS 7-206890  8/1995  Japan .

Primary Examiner—Kathleen K. Fonda
Attorney, Agent, or Firm—Oblon, Spivak, McClelland, Maier & Neustadt, P.C.

[57] ABSTRACT

A method for producing a sucrose fatty acid ester, which comprises subjecting sucrose and a lower alkyl ester of fatty acid to an ester exchange reaction in an organic solvent in the presence of an alkali catalyst to produce the corresponding sucrose fatty acid ester, wherein from 5 to 35 wt %, based on the starting material sucrose, of an alkali metal salt of a hydroxycarboxylic acid of the following formula (1) is present in the reaction system:

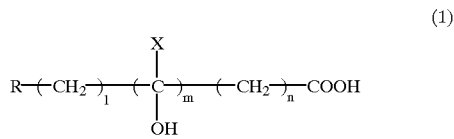

(1)

wherein R is a lower alkyl group or a carboxyl group, X is a hydrogen atom or a carboxyl group, each of l and n is 0 or 1, and m is 1 or 2.

5 Claims, No Drawings

METHOD FOR PRODUCING A SUCROSE FATTY ACID ESTER

BACKGROUND OF THE INVENTION

1. Field of the Invention

The present invention relates to a method for producing a sucrose fatty acid ester (hereinafter referred to simply as SE).

2. Discussion of Background

SE is widely used as a highly safe nonionic surfactant having both an excellent surface activating ability and a good biodegradation property for food products as well as for cosmetics, pharmaceuticals, cleaning agents and feed stuff.

As a method for producing SE, a method is known which comprises subjecting sucrose and a lower alkyl ester of fatty acid to an ester exchange reaction in an organic solvent such as N,N-dimethylformamide or dimethylsulfoxide in the presence of an alkali catalyst (JP-B-35-13102). The obtained reaction mixture contains the solvent, unreacted sucrose and the alkali catalyst, in addition to SE. To separate SE from this mixture, it is common to employ a method wherein upon deactivating the catalyst by an addition of an acid, the solvent is partially recovered, then by liquid-liquid extraction treatment with an organic solvent and water, SE is distributed to the organic solvent phase, and the unreacted sucrose and the rest of the solvent are distributed to the aqueous phase, and from the obtained organic solvent phase, the organic solvent is distilled off to separate and purify SE (for example, JP-B-48-21927, JP-B-48-35049, JP-A-50-29417, JP-A-50-130712). On the other hand, the unreacted sucrose and the reaction solvent recovered in the aqueous phase will be reused for the next reaction after removing water by distillation.

SE obtained by the above method usually contains a few % in total of a free fatty acid and an alkali metal salt of fatty acid (hereinafter referred to simply as a soap). These components have frequently given various influences over the physical properties or the function of SE, although their upper limits are stipulated in the regulations for food additives. For example, the free fatty acid remarkably lowers the water solubility of SE, and when SE has been used for oil-in-water type emulsification or dispersion solubilization, variation in the acid value has been a serious problem for the quality control.

SUMMARY OF THE INVENTION

Under these circumstances, the present inventors have conducted a study with an object to produce a SE product which has a low acid value constantly and which is excellent in dispersibility in water and oil-in-water type emulsification. The free fatty acid is considered to be formed in such a manner that the starting material lower alkyl ester of fatty acid is subjected to alkali hydrolysis during the reaction to form a soap, which is then freed by the subsequent extraction and purification step to form the free fatty acid as a by-product. Accordingly, it is considered possible to reduce the acid value of the product by suppressing formation of the free fatty acid as a by-product during the reaction of SE. It has now been found possible to accomplish the above object by carrying out the reaction of the conventional method for producing SE in the presence of a specific amount of an alkali metal salt of a hydroxycarboxylic acid.

Namely, the present invention provides a method for producing a sucrose fatty acid ester, which comprises subjecting sucrose and a lower alkyl ester of fatty acid to an ester exchange reaction in an organic solvent in the presence of an alkali catalyst to produce the corresponding sucrose fatty acid ester, wherein from 5 to 35 wt %, based on the starting material sucrose, of an alkali metal salt of a hydroxycarboxylic acid of the following formula (1) is present in the reaction system:

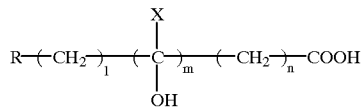

(1)

wherein R is a lower alkyl group or a carboxyl group, X is a hydrogen atom or a carboxyl group, each of 1 and n is 0 or 1, and m is 1 or 2.

DETAILED DESCRIPTION OF THE PREFERRED EMBODIMENTS

Now, the present invention will be described in detail.

In the present invention, the lower alkyl ester of fatty acid is usually an ester of a $C_{8-24}$ (such as caprylic acid, capric acid, lauric acid, myristic acid, palmitic acid, stearic acid, behenic acid, oleic acid, erucic acid, elaidic acid, lignocevic acid or ricinoleic acid), preferably $C_{10-22}$, saturated or unsaturated fatty acid with a $C_{1-4}$ lower alcohol (such as methanol, ethanol, propanol or butanol). These lower alkyl esters of fatty acids may be used alone or in combination as a mixture of two or more of them. The molar ratio of the lower alkyl ester of fatty acid to sucrose is usually from 0.2 to 2.5, preferably from 0.25 to 1.8. The average degree of substitution of the resulting SE will thereby be from 1 to 3, preferably from 1.2 to 2.7.

The organic solvent to be used in the present invention, may preferably be dimethylformamide or dimethylsulfoxide. Particularly preferred is dimethylsulfoxide from the viewpoint of the safety and the solubility of the starting material and SE.

The solvent is used usually in an amount of from 20 to 80 wt %, preferably from 50 to 70 wt %, based on the total amount of charge.

The reaction of the present invention is carried out in a non-aqueous system, and the alkali catalyst is present in a suspended state in the reaction system. As an alkali catalyst, an alkali metal hydride, an alkali metal hydroxide or an alkali metal salt of a weak acid may usually be employed. Whereas, in the present invention, an alkali metal carbonate (such as potassium carbonate or sodium carbonate) is particularly preferred with a view to suppressing hydrolysis of the lower alkyl ester of fatty acid as the starting material. The catalyst is added usually in an amount of from 0.05 to 0.5 mol % relative to the lower alkyl ester of fatty acid.

In the present invention, it is required that a specific small amount of an alkali metal salt of a hydroxycarboxylic acid of the above formula (1) is present in this reaction system. The hydroxycarboxylic acid of the formula (1) is an organic acid containing one or two hydroxyl groups and one to four carboxyl groups, preferably a monohydroxycarboxylic acid, more preferably a monohydroxymonocarboxylic acid. Specifically, an organic acid approved as a food additive, such as lactic acid, malic acid, citric acid or tartaric acid, is preferred from the viewpoint of safety. More preferred is lactic acid, malic acid or citric acid, and particularly preferred is lactic acid. The alkali metal may, for example, be potassium or sodium, preferably potassium. The amount of the alkali metal salt of a hydroxycarboxylic acid is usually from 5 to 35 wt %, preferably from 8 to 25 wt %, relative to the sucrose. If this amount is too small, the desired effect for reducing the acid value tends to be inadequate, and if it is too large, the reaction rate tends to be substantially low, such being undesirable. According to the study by the present inventors, the incorporated alkali metal salt of a hydroxycarboxylic acid can readily be separated from SE by liquid-liquid extraction in the purification step after the reaction and can readily be purged out of the system.

The reaction temperature is usually within a range of from 60 to 150° C., preferably from 80 to 120° C. The reaction pressure is usually from 0.1 to 50 Torr, preferably from 1 to 20 Torr. It is particularly preferred to carry out the reaction under a condition for boiling of the solvent, while removing an alcohol formed as a by-product, out of the reaction system. It is common that a condenser or a distillation column is connected to the top of the reactor, so that the solvent is separated from the alcohol formed as a by-product, and the reaction is carried out while refluxing the solvent in the reactor.

The reaction is carried out usually in such a manner that sucrose, an alkali metal salt of a hydroxycarboxylic acid and an organic solvent are charged into a reactor of an agitation tank type, dehydration treatment is carried out until the water content becomes not higher than 0.1 wt %, then the catalyst and a lower alkyl ester of fatty acid are added, whereupon the reaction is carried out with stirring at a predetermined reaction temperature and pressure for a predetermined period of time. The end point of the reaction is the time when the conversion of the lower alkyl ester of fatty acid has reached 99%. If the conversion of the lower alkyl ester of fatty acid has not reached 99%, even if the obtained reaction mixture is subjected to purification, the lower alkyl ester of fatty acid still remains in the final product SE, and such SE will not be suitable for use in food products.

After termination of the reaction, the alkali catalyst is usually neutralized and deactivated with an acid, and the solvent is distilled off. The acid used for deactivation is preferably an organic acid approved as a food additive, such as acetic acid propionic acid, butyric acid, benzoic acid, lactic acid, succinic acid, malic acid, tartaric acid or citric acid, taking into the safety into consideration. Particularly preferred is lactic acid taking into consideration also the corrosiveness to the apparatus, the solubility in water as well as the safety as an additive to a food product. SE in the obtained reaction mixture, is purified by a commonly known method, e.g. a method such as steam distillation after liquid-liquid extraction treatment with an organic solvent and an aqueous system.

Now, the present invention will be described in further detail with reference to Examples. However, it should be understood that the present invention is by no means restricted to such specific Examples. In the following description, the soap production ratio and the acid value were measured by the following methods.

1. Measurement of the Soap Production Ratio

From 0.5 to 1 g of the SE reaction mixture prior to neutralization by an addition of the acid, was accurately weighed and dissolved in 1 ml of pyridine containing 10 mg of dinonyl phthalate as an internal standard substance. Then, 0.7 ml of hexamethyldisilazane and 0.4 ml of trimethylchlorosilane were added thereto, and the mixture was vigorously shaken and then heated at 70° C. for 3 minutes. Then, the mixture was left to stand still at room temperature, and 2 μl of the supernatant was subjected to gas chromatograph (GC) under the following conditions.

Conditions for GC Measurement

Apparatus: GC-7A, manufactured by Shimazu Corporation

Column: Silicon OV 17 10% Uniport HP

Injection temperature: 310° C.

Column temperature:Initial 220° C. (4 min)
Final 300° C. (16 min)
Temperature raising rate: 5° C./min Detector: FID Internal standard solution: 10 mg of dinonyl phthalate/1 ml of pyridine Sample: 2 μl The soap production ratio is calculated by dividing the above measured value by a theoretical soap production amount of a case where all of the charged catalyst potassium became the soap.

2. Measurement of Acid Value

The acid value was measured by the following method in accordance with a standard oil and fat analytical method.

From about 10 to 20 g of a sample was accurately weighed and dissolved in 100 ml of a liquid mixture of tetrahydrofuran (THF)/ethanol/water=5/2/1 (vol. ratio). The solution as titrated with an alcoholic 0.1 N potassium hydroxide solution (potency: 1.003), and the acid value was calculated by the following formula:

$$\text{Acid value (mgKOH/g)} = 0.1 \times \text{potency} \times [(\text{titrated amount ml}) - \text{solvent blank ml})] \times 56.1/\text{sample g}$$

EXAMPLE 1

Into an agitation type reactor equipped with a heating jacket, 100 parts by weight of sucrose, 8 parts by weight of potassium lactate and 385 parts by weight of dimethylsulfoxide (hereinafter referred to simply as DMSO) as a solvent, were charged, and DMSO was refluxed for 15 minutes at 80° C. under 15 mmHg, whereupon 20 parts by weight of DMSO was distilled off to remove moisture in the reaction system. The water content in the system at that time was 0.05 wt %.

Then, 0.8 part by weight potassium carbonate and 56.5 parts by weight of methyl stearate were added, and the reaction was carried out at 90° C. under 20 mmHg for 7 hours while boiling DMSO with stirring at a rotational speed of 500 rpm. The final conversion of methyl stearate was 99.5%. The content of stearic acid soap in the obtained reaction mixture was quantitatively analyzed by the above method, whereby the soap production ratio of the catalyst potassium was 22 mol %.

1.8 parts by weight of a 50% lactic acid aqueous solution (0.85 time in equivalent to the catalyst potassium) was added to the reaction mixture to neutralize and deactivate the catalyst, and then 300 parts by weight of DMSO was distilled off by distillation at 90° C. under 20 mmHg. This concentrated mixture was dissolved in 825 parts by weight of 18 wt % water-containing isobutanol, and 700 parts by weight of pure water containing 1,750 ppm of potassium lactate was added thereto, followed by extraction treatment under atmospheric pressure at 60° C. by means of an extraction apparatus of mixer settler type.

Then, the isobutanol solution recovered from the mixer settler was supplied to a bottom of a rotary disk type extraction tower, and pure water containing 1,750 ppm of potassium lactate was supplied to the top, whereby a counter-current multistage extraction was carried out at 60° C. under atmospheric pressure. The supply ratio to the tower was 1.3 parts by weight of the isobutanol solution per part by weight of water. From the isobutanol solution recovered from the top of the tower, the solvent was distilled to obtain SE. The average degree of substitution of the obtained SE was 1.5, and the acid value was 1.7 mgKOH/g.

EXAMPLE 2

The reaction was carried out in the same manner as in Example 1 except that the amount of potassium lactate for the reaction was changed to 17 parts by weight per 100 parts by weight of sucrose. The final conversion of methyl stearate was 99%, and the soap production ratio of catalyst potassium was 17 mol %. Further, the average degree of substitution of SE obtained by purification was 1.5, and the acid value was 1.3 mgKOH/g.

EXAMPLE 3

In the same manner as in Example 1, 24 parts by weight of potassium lactate and 583 parts by weight of DMSO were charged, per 100 parts by weight of sucrose. Then, water was removed while distilling off 20 parts by weight of DMSO out of the system, and then 2.0 parts by weight of potassium carbonate and 141 parts by weight of methyl stearate were added, and the mixture was reacted for 12 hours. The final conversion of methyl stearate was 99%, and the soap production ratio of catalyst potassium was 15 mol %. Further, the average degree of substitution of SE obtained by purification was 2.1, and the acid value was 1.2 mgKOH/g.

Comparative Example 1

SE was produced in the same manner as in Example 1 except that potassium lactate was not added. The final conversion of methyl stearate was 99%, and the soap production ratio of catalyst potassium was 40 mol %. As a result of purification conducted in the same manner, the average degree of substitution of SE thereby obtained was 1.5, and the acid value was 2.4 mgKOH/g.

Comparative Example 2

The reaction was carried out in the same manner as in Example 1 except that the amount of potassium lactate was changed to 3 parts by weight per 100 parts by weight of sucrose. The final conversion of methyl stearate was 99%, and the soap conversion ratio of catalyst potassium was 38 mol %. As a result of purification carried out in the same manner, the average degree of substitution of SE thereby obtained was 1.5, and the acid value was 2.2 mgKOH/g.

Comparative Example 3

SE was produced in the same manner as in Example 3 except that potassium lactate was not added. The final conversion of methyl stearate was 99%, and the soap production ratio of catalyst potassium was 36 mol %. As a result of purification carried out in the same manner, the average degree of substitution of SE thereby obtained was 2.1, and the acid value was 2.2 mgKOH/g.

Comparative Example 4

The reaction was carried out in the same manner as in Example 1 except that the amount of potassium lactate was changed to 50 parts by weight per 100 parts by weight of sucrose, whereby the conversion of methyl stearate after 7 hours of the reaction time was 90%.

Comparative Example 5

The reaction was carried out in the same manner as in Example 3 except that the amount potassium lactate was changed to 50 parts by weight per 100 parts by weight of sucrose, whereby the conversion of methyl stearate after 12 hours of the reaction time was 92%.

The dispersibility in water and the oil-in-water type (O/W type) emulsification ability of the SE product obtained by these experiments were evaluated in accordance with the following methods.

Dispersibility in Water 1 g of SE was dispersed in 99 g of water at 25° C., and the dispersion was stirred for 5 minutes in a constant temperature tank of 70° C., whereupon the dispersibility in water was evaluated under the following standards.

○: Readily uniformly dispersed.

Δ: Slightly hardly dispersible and turbidity is substantial.

X: Very hardly dispersible, insoluble substances remain.

Oil-in-Water Type Emulsification Ability

Formulation:

| | |
|---|---|
| SE | 2.0 parts by weight |
| Oil component (soybean oil or liquid paraffin) | 30.0 parts by weight |
| Water | 68.0 parts by weight |

Method:

2 g of SE was dispersed and dissolved in 68 g of water at a temperature of from 60 to 80° C., and while stirring this aqueous phase at 3,000 rpm by TK homomixer (manufactured by Tokushu Kika K.K.), the oil component of 60° C. was slowly added. Then, the mixture was further stirred for 5 minutes at 10,000 rpm for emulsification. The emulsified product was rapidly cooled in ice water and then stored to stand still at 25° C. for 24 hours.

Evaluation:

The stability of the emulsion was evaluated by the water-separation ratio as defined by the following formula:

Water-separation ratio (vol %)=volume of water separated from the emulsion/total volume of the emulsified product ×100

The smaller the water-separation ratio, the more stable the emulsion.

Standards:

○: Water-separation ratio of less than 5%

Δ: Water-separation ratio of from 5 to 10%

X: water-separation ratio of higher than 10% The above results are shown in Table 1.

TABLE 1

| | Reaction conditions | | | | | |
|---|---|---|---|---|---|---|
| | Methyl-stearate charge (molar ratio to sucrose) | Amount of potassium lactate (wt % to sucrose) | Soap production ratio (mol %) | Acid value of SE (mgKOH/g) | Dispersibility in water | O/W type emulsification ability |
| Example 1 | 0.67 | 8 | 22 | 1.7 | ○ | ○ |
| Example 2 | 0.67 | 17 | 17 | 1.3 | ○ | ○ |
| Example 3 | 1.67 | 24 | 15 | 1.2 | ○ | ○ |
| Comparative Example 1 | 0.67 | 0 | 40 | 2.4 | Δ | X |
| Comparative Example 2 | 0.67 | 3 | 38 | 2.2 | Δ | Δ |
| Comparative Example 3 | 1.67 | 0 | 36 | 2.2 | X | Δ |
| Comparative Example 4 | 0.67 | 50 | — | — | — | — |
| Comparative Example 5 | 1.67 | 50 | — | — | — | — |

According to the present invention, a certain small amount of an alkali metal salt of a hydroxycarboxylic acid is present in the reaction system for the production of SE, whereby it is possible to constantly produce SE which has a low acid value and which is excellent in the dispersibility in water and the oil-in-water type emulsification ability. The reason is not clearly understood, but it is considered that the alkali metal of a hydroxycarboxylic acid gives an influence over the solubility of the alkali catalyst in the reaction system, thereby to suppress production of a soap as a by-product.

Further, the alkali metal salt of a hydroxycarboxylic acid added to the reaction system, can easily be removed in the step for purifying SE from the reaction mixture, and it presents no adverse effect to the commercial value of the obtained SE.

What is claimed is:

1. A method for producing a sucrose fatty acid ester, which comprises subjecting sucrose and a lower alkyl ester of fatty acid to an ester exchange reaction in an organic solvent in the presence of an alkali catalyst to produce the corresponding sucrose fatty acid ester, wherein from 5 to 35 wt %, based on the starting material sucrose, of an alkali metal salt of a hydroxycarboxylic acid of the following formula (1) is present in the reaction system:

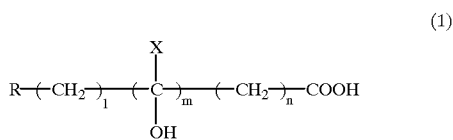

(1)

wherein R is a lower alkyl group or a carboxyl group, X is a hydrogen atom or a carboxyl group, each of l and n is 0 or 1, and m is 1 or 2.

2. The method according to claim 1, wherein the hydroxycarboxylic acid is at least one member selected from the group consisting of lactic acid, malic acid and citric acid.

3. The method according to claim 1, wherein the amount of the alkali metal salt of a hydroxycarboxylic acid is from 8 to 25 wt %, based on the starting material sucrose.

4. The method according to claim 1, wherein the alkali catalyst is an alkali metal carbonate.

5. The method according to claim 1, wherein the organic solvent is dimethylsulfoxide.

* * * * *